(12) United States Patent
Karlsson et al.

(10) Patent No.: US 10,131,718 B2
(45) Date of Patent: Nov. 20, 2018

(54) CROSS-LINKED HYALURONIC ACID GRAFTED WITH DEXTRAN

(71) Applicant: GALDERMA S.A., Cham (CH)

(72) Inventors: Anders Karlsson, Storvreta (SE); Hotan Mojarradi, Uppsala (SE)

(73) Assignee: GALDERMA S.A., Cham (CH)

( * ) Notice: Subject to any disclaimer, the term of this patent is extended or adjusted under 35 U.S.C. 154(b) by 158 days.

(21) Appl. No.: 15/314,168

(22) PCT Filed: May 29, 2015

(86) PCT No.: PCT/EP2015/062010
§ 371 (c)(1),
(2) Date: Nov. 28, 2016

(87) PCT Pub. No.: WO2015/181369
PCT Pub. Date: Dec. 3, 2015

(65) Prior Publication Data
US 2018/0244807 A1  Aug. 30, 2018

Related U.S. Application Data

(60) Provisional application No. 62/004,285, filed on May 29, 2014.

(51) Int. Cl.
| | |
|---|---|
| *C08B 37/02* | (2006.01) |
| *C08B 37/08* | (2006.01) |
| *A61K 8/73* | (2006.01) |
| *C08J 3/075* | (2006.01) |
| *A61Q 19/08* | (2006.01) |
| *C08J 3/24* | (2006.01) |
| *A61L 27/20* | (2006.01) |
| *A61L 27/52* | (2006.01) |

(52) U.S. Cl.
CPC .......... *C08B 37/0072* (2013.01); *A61L 27/20* (2013.01); *A61L 27/52* (2013.01); *A61Q 19/08* (2013.01); *C08B 37/0021* (2013.01); *C08J 3/075* (2013.01); *C08J 3/24* (2013.01); *A61K 8/73* (2013.01); *C08J 2305/02* (2013.01); *C08J 2305/08* (2013.01)

(58) Field of Classification Search
CPC .......... A61K 8/73; A61K 8/735; A61L 27/20; A61L 27/52; A61Q 19/08; C08L 5/02; C08L 5/08; C08J 3/075; C08B 37/0021; C08B 37/0072
See application file for complete search history.

(56) References Cited

U.S. PATENT DOCUMENTS

2010/0136070 A1  6/2010  Dobak et al.

FOREIGN PATENT DOCUMENTS

| WO | WO 97/04012 A1 | 2/1997 |
| WO | WO 03/047462 A1 | 6/2003 |
| WO | WO 2011/059325 A2 | 5/2011 |
| WO | WO 2014/055532 A2 | 4/2014 |
| WO | WO 2014/198683 A2 | 12/2014 |

OTHER PUBLICATIONS

International Search Report (PCT/ISA/210) dated Aug. 6, 2015, by the European Patent Office as the International Searching Authority for International Application No. PCT/EP2015/062010.
Written Opinion (PCT/ISA/237) dated Aug. 6, 2015, by the European Patent Office as the International Searching Authority for International Application No. PCT/EP2015/062010.

*Primary Examiner* — Leigh C Maier
(74) *Attorney, Agent, or Firm* — Buchanan Ingersoll & Rooney P.C.

(57) ABSTRACT

A hyaluronic acid product is comprising a cross-linked hyaluronic acid and one or more dextran molecules. The hyaluronic acid is cross-linked by ether bonds, and the one or more dextran molecules are covalently grafted to the cross-linked hyaluronic acid.

33 Claims, 3 Drawing Sheets

CROSS-LINKED HYALURONIC ACID GRAFTED WITH DEXTRAN

TECHNICAL FIELD OF THE INVENTION

The present invention relates to the field of hydrogels containing cross-linked polysaccharides and the use of such hydrogels in medical and/or cosmetic applications. More specifically, the present invention deals with cross-linked hyaluronic acid grafted with dextran.

BACKGROUND OF THE INVENTION

One of the most widely used biocompatible polymers for medical use is hyaluronic acid (HA). It is a naturally occurring polysaccharide belonging to the group of glycosaminoglycans (GAGs). Hyaluronic acid and the other GAGs are negatively charged heteropolysaccharide chains which have a capacity to absorb large amounts of water. Hyaluronic acid and products derived from hyaluronic acid are widely used in the biomedical and cosmetic fields, for instance during viscosurgery and as a dermal filler.

Water-absorbing gels, or hydrogels, are widely used in the biomedical field. They are generally prepared by chemical cross-linking of polymers to infinite networks. While native hyaluronic acid and certain cross-linked hyaluronic acid products absorb water until they are completely dissolved, cross-linked hyaluronic acid gels typically absorb a certain amount of water until they are saturated, i.e. they have a finite liquid retention capacity, or swelling degree.

Since hyaluronic acid is present with identical chemical structure except for its molecular mass in most living organisms, it gives a minimum of reactions and allows for advanced medical uses. Cross-linking and/or other modifications of the hyaluronic acid molecule is necessary to improve its duration in vivo. Furthermore, such modifications affect the liquid retention capacity of the hyaluronic acid molecule. As a consequence thereof, hyaluronic acid has been the subject of many modification attempts.

SUMMARY OF THE INVENTION

It is an object of the present invention to provide a cross-linked hyaluronic acid product suitable for use as a dermal filler.

It is a further object of the present invention to provide a cross-linked hyaluronic acid product suitable having improved durability in use as a dermal filler.

It is a further object of the present invention to provide a cross-linked hyaluronic acid product suitable having reduced swelling.

For these and other objects that will be evident from this disclosure, the present invention provides according to a first aspect a hyaluronic acid product comprising a cross-linked hyaluronic acid and one or more dextran molecules, wherein the hyaluronic acid is cross-linked by ether bonds and wherein the one or more dextran molecules are covalently grafted to the cross-linked hyaluronic acid.

The term cross-linking as used herein refers to a reaction involving sites or groups on existing macromolecules or an interaction between existing macromolecules that results in the formation of a small region in a macromolecule from which at least four chains emanate. A reaction of a reactive chain end of a linear macromolecule with an internal reactive site of another linear macromolecule results in the formation of a branch point or graft, but is not regarded as a cross-linking reaction.

The term grafting as used herein refers to a reaction in which one or more species of block are connected to the main chain of a macromolecule as side-chains having constitutional or configurational features that differ from those in the main chain.

The inventors have surprisingly found that it is possible to graft dextran to a hyaluronan hydrogel with high conversion. This finding was unexpected since the cross-linked hyaluronic acid network would be expected to prevent diffusion of dextran leading to a reduced efficiency of grafting.

Hyaluronic acid products according to the present invention, comprising a cross-linked hyaluronic acid with one or more dextran molecules grafted, display several advantageous and surprising properties, e.g. including improved stability to thermal, hydrolytic, radical and enzymatic degradation resulting in improved durability in use as a dermal filler, and decreased swelling capacity. Reduced swelling capacity means that harder gels can be produced, without increasing the amount of cross-linker in the hyaluronic acid.

The cross-linked hyaluronic acid products according to the invention can be used, e.g., as injectable compositions for cosmetic or medical surgery, like dermal filling and body contouring. The cross-linked hyaluronic acid products according to the invention, combining hyaluronic acid with dextran, exhibit decreased swelling compared to hyaluronic acid products without dextran. This is useful, since it means that harder gels can be produced, without increasing the amount of cross-linker in the hyaluronic acid. The cross-linked hyaluronic acid products according to the invention have also been found to have a better thermal stability as well as better stability to radical and enzymatic degradation as compared hyaluronic acid products without dextran. A possible explanation is that the hyaluronic acid backbone is protected by the dextran. This leads to an improved of durability in vivo of the cross-linked hyaluronic acid products according to the invention as compared hyaluronic acid products without dextran.

In a preferred embodiment, the dextran is attached to the hyaluronic acid by amide bonds. The use of amide bonds in the dextran-hyaluronic acid graft has been found to be advantageous compared to e.g. ester bonds, since the amide bond is more stable to degradation in vivo.

It is advantageous to graft the dextran molecules on already cross-linked hyaluronic acid, which may already be prepared in a desirable form having defined physico-chemical properties. This allows for a significant modification of cross-linked HA with dextrans without inducing depolymerisation of the cross-linked HA.

According to a second aspect illustrated herein, there is provided a process of preparing a hyaluronic acid product comprising a cross-linked hyaluronic acid and one or more functionalized dextran molecules, the process comprising the steps of:
(a) providing a cross-linked hyaluronic acid and one or more functionalized dextran molecules;
(b) covalently grafting one or more functionalized dextran molecules to the cross-linked hyaluronic acid.

The dextran molecules are covalently grafted to the cross-linked hyaluronic acid. In preferred embodiments the dextran molecules are grafted to the cross-linked hyaluronic acid by single end-point attachment. In order to enable the covalent grafting the dextran molecules are functionalized with a suitable reactive functional group. The dextran molecules may for example be provided with a linker having an amino group, in order to enable grafting to the cross-linked hyaluronic acid by amide bonds.

Since the nature of the product obtainable by the processes according to the invention is complex, the product may also be defined as being the result of these processes. According to another aspect illustrated herein, there is provided a cross-linked hyaluronic acid product comprising hyaluronic acid and dextran, obtainable by the process described herein.

The cross-linked hyaluronic acid products of the present disclosure may for example be used in injectable formulations for treatment of soft tissue disorders, including but not limited to, corrective and aesthetic treatments.

The cross-linked hyaluronic acid products of the present disclosure may for example be used in injectable formulations for cosmetic surgery, e.g. dermal filling, body contouring and facial contouring, in medical surgery, e.g. dermal filling, body contouring, prevention of tissue adhesion, formation of channels, incontinence treatment, and orthopaedic applications, and for hydrating and/or vitalizing the skin.

According to aspects illustrated herein, there is provided a method of cosmetically treating skin, which comprises administering to the skin a cross-linked hyaluronic acid product as described herein.

The cross-linked hyaluronic acid product may also be provided in an injectable dermal aesthetic or pharmaceutical formulation.

Other aspects and preferred embodiments of the present invention will be evident from the following detailed disclosure of the invention and the appended claims.

DETAILED DESCRIPTION OF THE INVENTION

Figure 1:
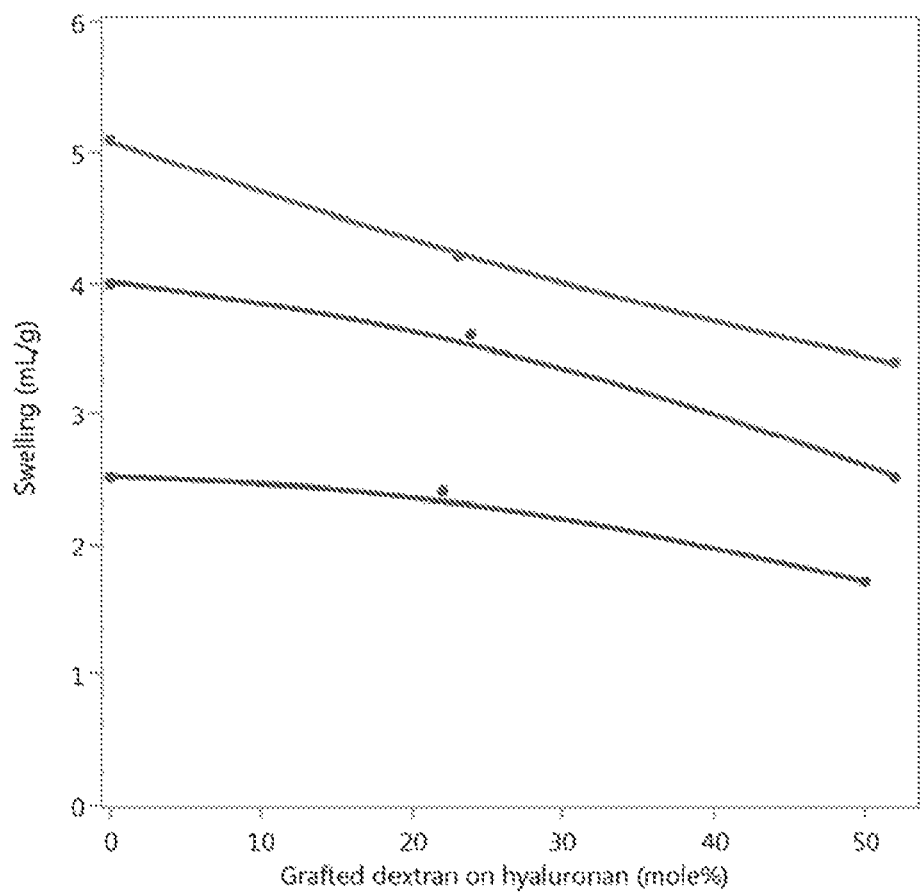
FIG. 1 Diagram illustrating how the swelling of the hyaluronic acid gel is decreased with increasing grafting with dextran.

The inventive hyaluronic acid (hyaluronic acid is also referred to herein as "HA" or "hyaluronan") product comprises a cross-linked hyaluronic acid and one or more dextran molecules, wherein the hyaluronic acid is cross-linked by ether bonds and wherein the one or more dextran molecules are covalently grafted to the cross-linked hyaluronic acid.

The hyaluronic acid product may be present in an aqueous solution, but it may also be present in dried or precipitated form, e.g. in ethanol. The hyaluronic acid product is preferably injectable.

The hyaluronic acid product may be present in the form of a gel (also referred to herein as "hydrogel"). The total amount of polysaccharide in the gel is preferably is in the range 5-150 mg/mL, more preferably in the range 10-100 mg/mL.

The molar amount of dextran grafted to the cross-linked hyaluronic acid is in the range of 0.1-99%, preferably in the range 1-60%.

The hyaluronic acid products are evaluated by their swelling, i.e. their ability to absorb water. Swelling is expressed as the amount of water (or saline) in mL that one gram of dry product can absorb. The swelling can also be measured on a gel and be expressed in mL per gram gel. The swelling of the hyaluronic acid product is preferably in the range 0.5-10 mL/g, more preferably in the range 1-5 mL/g.

The inventive hyaluronic acid product may be in the form of gel particles, strings, discs, etc. In a preferred embodiment, the cross-linked hyaluronic acid is in the form of gel particles. The gel particles preferably have an average swelled size (unless specified otherwise, all particle sizes given herein refer to weight average particle size) in the range of 0.01-5 mm, preferably 0.1-1 mm, such as 0.2-0.5 mm or 0.5-0.8 mm. According to some embodiments, the cross-linked hyaluronic acid is in the form of gel particles having an average size in the range of 0.01-5 mm, preferably 0.1-1 mm.

According to some embodiments, the one or more dextran molecules and the disaccharides of the cross-linked hyaluronic acid have a molar ratio of 0.1-99%, such as 0.1-60%, such as 1-60%, or such as 1-20%. A molar ratio of 50% means that half of the HA disaccharide have a dextran chain grafted.

According to some embodiments, the dextran molecules have an average molecular weight of less than 10 kDa, preferably less than 5 kDa.

According to some embodiments, the dextran molecules are covalently linked to the hyaluronic acid by single end-point attachment. Single end-point attachment means that the dextran is attached to the hyaluronic acid only via an end residue of the dextran molecule, preferably via the reducing end of the dextran molecule. According to some embodiments, the dextran molecules are covalently linked to the hyaluronic acid by single end-point attachment via a bi- or polyfunctional linker between the reducing end of dextran and a carboxyl group of hyaluronic acid.

According to some embodiments the dextran molecule contains a linker having an amino, hydrazide, carbazate, semicarbazide, thiosemicarbazide, thiocarbazate or aminooxy functional group, and wherein the functional group of the linker forms a covalent bond with a carboxyl group of the cross-linked hyaluronic acid.

According to some embodiments, the bi- or polyfunctional linker comprises at least two functional groups independently selected from amino, hydrazide, carbazate, semicarbazide, thiosemicarbazide, thiocarbazate or aminooxy. According to some embodiments, the bi- or polyfunctional linker is a diamine or a dihydrazide. According to some embodiments, the bi- or polyfunctional linker is a hexamethylene diamine, 2,2'-(ethylenedioxy)bis(ethylamine), O,O'-1,3-Propanediylbis-hydroxylamine, adipic acid dihydrazide or spermidine.

Unless otherwise provided, the term "hyaluronic acid" encompasses all variants and combinations of variants of hyaluronic acid, hyaluronate or hyaluronan, of various chain lengths and charge states, as well as with various chemical modifications. That is, the term also encompasses the various hyaluronate salts of hyaluronic acid with various counter ions, such as sodium hyaluronate. Various modifications of the hyaluronic acid are also encompassed by the term, such as oxidation, e.g. oxidation of —$CH_2OH$ groups to —CHO and/or —COOH; periodate oxidation of vicinal hydroxyl groups, optionally followed by reduction, e.g. reduction of —CHO to —$CH_2OH$ or coupling with amines to form imines followed by reduction to secondary amines; sulphation; deamidation, optionally followed by deamination or amide formation with new acids; esterification; and deacetylation. Other examples of modifications are isourea, hydrazide, bromocyan, monoepoxide and monosulfone couplings.

The hyaluronic acid can be obtained from various sources of animal and non-animal origin. Sources of non-animal origin include yeast and preferably bacteria. The molecular weight of a single hyaluronic acid molecule is typically in the range of 0.1-10 MDa, but other molecular weights are possible.

In certain embodiments, the concentration of the cross-linked hyaluronic acid is in the range of 1 to 100 mg/ml. In some embodiments the concentration of the cross-linked hyaluronic acid is in the range of 2 to 50 mg/ml. In specific embodiments the concentration of the cross-linked hyaluronic acid is in the range of 5 to 30 mg/ml or in the range of 10 to 30 mg/ml.

Cross-linked hyaluronic acid comprises cross-links between the hyaluronic acid chains, which creates a continuous network of hyaluronic acid molecules which is held together by the covalent cross-links, physical entangling of the hyaluronic acid chains and various interactions, such as electrostatic interactions, hydrogen bonding and van der Waals forces.

The cross-linked hyaluronic acid product is preferably biocompatible. This implies that no, or only very mild, immune response occurs in the treated individual. That is, no or only very mild undesirable local or systemic effects occur in the treated individual.

The cross-linked hyaluronic acid product according to the invention may be a gel, or a hydrogel. That is, it can be regarded as a water-insoluble, but substantially dilute cross-linked system of hyaluronic acid molecules when subjected to a liquid, typically an aqueous liquid.

The gel contains mostly liquid by weight and can e.g. contain 90-99.9% water, but it behaves like a solid due to a three-dimensional cross-linked hyaluronic acid network within the liquid. Due to its significant liquid content, the gel is structurally flexible and similar to natural tissue, which makes it very useful as a scaffold in tissue engineering and for tissue augmentation.

Cross-linking of the hyaluronic acid may be achieved by modification with a cross-linking agent. The hyaluronic acid concentration and the extent of cross-linking affects the mechanical properties, e.g. the elastic modulus G', and stability properties of the gel. Cross-linked hyaluronic acid gels are often characterized in terms of "degree of modification". The degree of modification of hyaluronic acid gels generally range between 0.1 and 15 mole %. The degree of modification (mole %) describes the amount of cross-linking agent(s) that is bound to HA, i.e. molar amount of bound cross-linking agent(s) relative to the total molar amount of repeating HA disaccharide units. The degree of modification reflects to what degree the HA has been chemically modified by the cross-linking agent. Reaction conditions for cross-linking and suitable analytical techniques for determining the degree of modification are all well known to the person skilled in the art, who easily can adjust these and other relevant factors and thereby provide suitable conditions to obtain a degree of modification in the range of 0.1-2% and verify the resulting product characteristics with respect to the degree of modification. A BDDE (1,4-butanediol diglycidylether) cross-linked hyaluronic acid gel may for example be prepared according to the method described in Examples 1 and 2 of published international patent application WO 9704012.

In a preferred embodiment, the cross-linked hyaluronic acid is present in the form of a gel cross-linked by a cross-linking agent, wherein the concentration of said hyaluronic acid is in the range of 10 to 30 mg/ml, and the degree of modification with said cross-linking agent is in the range of 0.1 to 2 mole %.

Hyaluronic acid gels may also comprise a portion of hyaluronic acid which is not cross-linked, i.e not bound to the three-dimensional cross-linked hyaluronic acid network. However, it is preferred that at least 50% by weight, preferably at least 60% by weight, more preferably at least 70% by weight, and most preferably at least 80% by weight, of the hyaluronic acid in a gel composition form part of the cross-linked hyaluronic acid network.

The hyaluronic acid may be present in the form of particles, strings, discs, etc. In a preferred embodiment, the cross-linked hyaluronic acid is in the form of gel particles. The gel particles preferably have an average size in the range of 0.01-5 mm, preferably 0.1-1 mm, such as 0.2-0.5 mm or 0.5-0.8 mm.

The hyaluronic acid chains are cross-linked to each other via a linker which is derived from a bi- or polyfunctional cross-linking agent. The bi- or polyfunctional cross-linking agent of the hyaluronic acid composition connects the hyaluronic acid chains to each other. The bi- or polyfunctional cross-linking agent further acts as a spacer between the hyaluronic acid chains.

The bi- or polyfunctional cross-linking agent comprises two or more functional groups capable of reacting with functional groups of the hyaluronic acid, resulting in the formation of covalent bonds. The bi- or polyfunctional cross-linking agent may for example selected from the group consisting of divinyl sulfone, diepoxides and multiepoxides.

A preferred type of bi- or polyfunctional cross-linking agent is a bis- or polyepoxide, such as a diglycidyl ether. According to an embodiment, the bi- or polyfunctional cross-linking agent comprises two or more glycidyl ether functional groups. The glycidyl ether functional groups react with primary hydroxyl groups of the hyaluronic acid, resulting in the formation of ether bonds. It follows that when a diglycidyl ether cross-linking agent reacts with the primary hydroxyl groups of hyaluronan, two ether bonds are formed with an intermediate spacer remaining from the cross-linking agent, Preferred bi- or polyfunctional cross-linking agent for cross-linking the hyaluronic acid chains include 1,4-butanediol diglycidyl ether (BDDE), 1,2-bis(2,3-epoxypropoxy)ethylene (EGDGE) and ethylene glycol diglycidyl ether (EGDE), 1,2-ethanediol diglycidyl ether (EDDE) and diepoxyoctane. A particularly preferred bi- or polyfunctional cross-linking agent is BDDE.

The dextran may be of any average molecular weight (unless otherwise specified, all average molecular weights of dextran given herein refer to number average molecular weights, $M_n$), typically in the range of 0.2 to 3000 kDa In some embodiments it is preferred that the dextran has a lower molecular weight, such as less than 100 kDa, less than 50 kDa, less than 25 kDa, less than 10 kDa or less than 5 kDa. The dextran has a molecular weight of more than 0.2 kDa, preferably mer than 0.5 kDa. In some embodiments, the dextran has a molecular weight in the range of 10-100 kDa or in the range of 10-50 kDa. In some preferred embodiments, the dextran has a molecular weight in the range of 0.5-10 kDa or in the range of 0.5-5 kDa. In one preferred embodiment, the dextran has an average molecular weight in the range of 0.5-3 kDa.

Dextrans are often chemically modified in order to improve their solubility in water and/or to optimize their performance in a specific application. The term dextran as used herein is also intended to encompass the functionally equivalent variants or derivatives thereof.

The cross-linked hyaluronic acid product according to the invention is preferably biocompatible. This implies that no, or only very mild, immune response occurs when the product is introduced into the tissue of an individual. That is, no or only very mild undesirable local or systemic effects occur in the treated individual.

The cross-linked hyaluronic acid products of the present disclosure may for example be used in injectable formulations for treatment of soft tissue disorders, including but not limited to, corrective and aesthetic treatments.

The cross-linked hyaluronic acid products of the present disclosure may for example be used in injectable formulations for cosmetic surgery, e.g. dermal filling, body contouring and facial contouring, in medical surgery, e.g. dermal filling, body contouring, prevention of tissue adhesion, formation of channels, incontinence treatment, and orthopaedic applications, and for hydrating and/or vitalizing the skin.

The cross-linked hyaluronic acid product may also be provided in an injectable dermal aesthetic or pharmaceutical formulation.

The cross-linked hyaluronic acid products of the present disclosure may also be used in injectable formulations for the transport or administration and slow or controlled release of various pharmaceutical or cosmetic substances.

The injectable formulations may optionally include one or more other pharmaceutically acceptable components, including, but not limited to, buffers, preservatives, tonicity adjusters, salts, antioxidants, osmolality adjusting agents, emulsifying agents, wetting agents, sweetening or flavoring agents, and the like.

The injectable formulations may optionally include a pharmaceutically effective amount of an anesthetic agent. The anesthetic agent may be a local anesthetic agent, e.g. an aminoamide local anesthetic or aminoester local anesthetic. Examples of anesthetic agents include, but are not limited to, lidocaine, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cyclomethycaine, dibucaine, dimethisoquin, dimethocaine, diperodon, dicyclomine, ecgonidine, ecgonine, ethyl chloride, etidocaine, β-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, combinations thereof, and salts thereof. Examples of aminoester local anesthetics include, but are not limited to procaine, chloroprocaine, cocaine, cyclomethycaine, dimethocaine (larocaine), propoxycaine, procaine (novocaine), proparacaine, tetracaine (amethocaine). Non-limiting examples of aminoamide local anesthetics include articaine, bupivacaine, cinchocaine (dibucaine), etidocaine, levobupivacaine, lidocaine (lignocaine), mepivacaine, piperocaine, prilocaine, ropivacaine, trimecaine, or a combination thereof.

The cross-linked hyaluronic acid product, or injectable pharmaceutical formulation comprising a cross-linked hyaluronic acid product, as described herein may be used for improving the appearance of skin, filling wrinkles or contouring the face or body of a subject.

The cross-linked hyaluronic acid product, or injectable pharmaceutical formulation comprising a cross-linked hyaluronic acid product, as described herein may advantageously be used as a dermal filler.

The cross-linked hyaluronic acid product, or injectable pharmaceutical formulation comprising a cross-linked hyaluronic acid product, as described herein may be used in a method of cosmetically treating skin, which comprises administering to the skin a cross-linked hyaluronic acid product as described herein.

The cross-linked hyaluronic acid product, or injectable pharmaceutical formulation comprising a cross-linked hyaluronic acid product, as described herein may also be used in the treatment of a joint disorder by intraarticular injection.

The above described uses of the cross-linked hyaluronic acid product, or injectable pharmaceutical formulation comprising a cross-linked hyaluronic acid product, may be medical procedures or purely cosmetic non-medical procedures.

In a preferred embodiment, the dextran molecules are grafted to the cross-linked hyaluronic acid by amide bonds. The dextran molecules are functionalized, e.g. aminated, in order to enable grafting to the cross-linked hyaluronic acid by amide bonds. Thus, the present invention allows for a mild coupling reaction producing an amide bond between the dextran and cross-linked hyaluronic acid with defined physico-chemical properties, e.g. in particle form. The use of amide bonds in the dextran-hyaluronic acid linkage (graft) has been found to be advantageous compared to e.g. ester bonds, since the amide bond is more stable to degradation in vivo. The resulting cross-linked hyaluronic acid product has useful stability properties and is thus suitable as a dermal filler as well as for slow-release applications. Another advantage is that the grafting of dextran molecules via an amide bond to ether cross-linked hyaluronic acid allows for a significant modification of the cross-linked hyaluronic acid with dextran without inducing depolymerisation thereof.

The hyaluronic acid product can be prepared by a process comprising the steps of:
(a) providing a cross-linked hyaluronic acid and one or more functionalized dextran molecules;
(b) covalently grafting one or more functionalized dextran molecules to the cross-linked hyaluronic acid.

According to some embodiments, the cross-linked hyaluronic acid in step (a) is in the form of gel particles having an average size in the range of 0.01-5 mm, preferably 0.1-1 mm.

According to some embodiments, the one or more dextran molecules and the disaccharides of the cross-linked hyaluronic acid of the resulting hyaluronic acid product have a molar ratio of 0.1-99%, preferably 1-60%.

According to some embodiments, the dextran molecules provided in step (a) have an average molecular weight of less than 10 kDa, preferably less than 5 kDa.

According to some embodiments, the dextran molecules are covalently linked to the hyaluronic acid by single end-point attachment. According to some embodiments, the dextran molecules are covalently linked to the hyaluronic acid by single end-point attachment via a bi- or polyfunc- According to some embodiments, step (a) of the process further comprises functionalizing the dextran molecules at the reducing end with a bi- or polyfunctional linker having at least one functional group available for linking the dextran molecules to a carboxyl group of the cross-linked hyaluronic acid. This process is generally described in Reaction scheme 1.

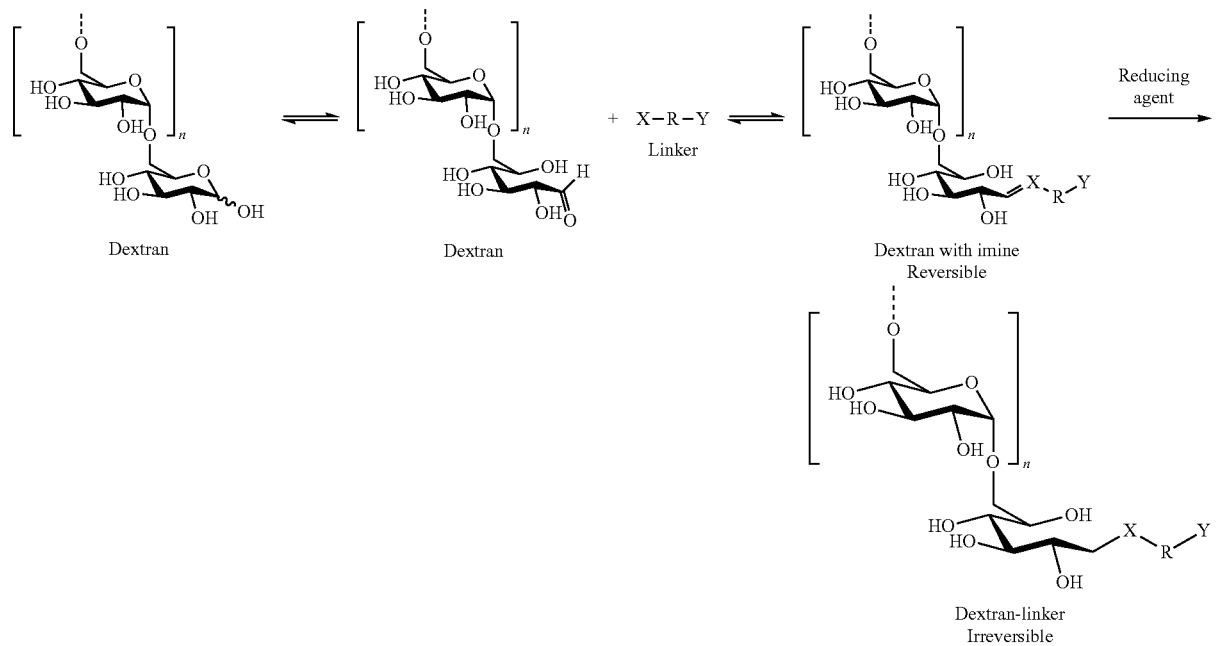

tional linker between the reducing end of dextran and a carboxyl group of hyaluronic acid.

According to some embodiments, the functionalized dextran molecules provided in step (a) are functionalized at the reducing end with a bi- or polyfunctional linker having at least one functional group available for linking the dextran molecules to a carboxyl group of the cross-linked hyaluronic acid.

According to some embodiments, the bi- or polyfunctional linker comprises at least two functional groups independently selected from amino, hydrazide, carbazate, semicarbazide, thiosemicarbazide, thiocarbazate or aminooxy. According to some embodiments, the bi- or polyfunctional linker is a diamine or a dihydrazide. According to some embodiments, the bi- or polyfunctional linker is hexamethylene diamine, 2,2'-(ethylenedioxy)bis(ethylamine), O,O'-1,3-Propanediylbis-hydroxylamine, adipic acid dihydrazide or spermidine.

According to some embodiments, the one or more functionalized dextran molecules of step (a) contain a linker having an amino, hydrazide, carbazate, semicarbazide, thiosemicarbazide, thiocarbazate or aminooxy functional group, and wherein the functional group of the linker forms a covalent bond with a carboxyl group of the cross-linked hyaluronic acid.

The bi- or polyfunctional linker can have the general formula X—R—Y, wherein X is a functional group capable of forming a bond with the reducing end of dextran and wherein X and Y can be the same functional group or two different functional groups. R is a suitable spacer group, and may for example include, but is not limited to, alkyl, alkoxy, ether, thioether or the like. The functional group X is able to react with the aldehyde group of the open-ring form of dextran in order to form an imine, which can then be reduced by a reducing agent to form a stable bond. The linker can only react on one site on dextran since it only has one aldehyde group at the reducing end group, thus making the reaction highly specific. The functional group X may for example be amine, hydrazide, carbazate, semicarbazide, thiosemicarbazide, thiocarbazate or aminooxy. The reducing agent may for example be $NaCNBH_3$, $NaBH_4$, STAB (sodium triacetoxyborohydride), or 2-picoline borane complex. The functional group Y can optionally be protected with a suitable protecting group (e.g. a tert-butyloxycarbonyl (boc)) during the reaction with the reducing end of dextran, and deprotected before the coupling to the carboxylic group of the cross-linked hyaluronic acid. Suitable reaction conditions for functionalizing the dextran molecules include pH in the range of 3-11, reaction time in the range of 1-48 h, reaction temperature in the range of 20-60° C., molar ratio of linker to dextran in the range of 1:1 to 50:1, and molar ratio of reducing agent to dextran in the range of 1:1 to 50:1.

The functionalized dextran (dextran-linker) can be grafted to cross-linked hyaluronic acid via the free functional group Y of the linker, for example using triazine- or carbodiimide-mediated amidation. The process is generally described in Reaction scheme 2.

Reaction scheme 2

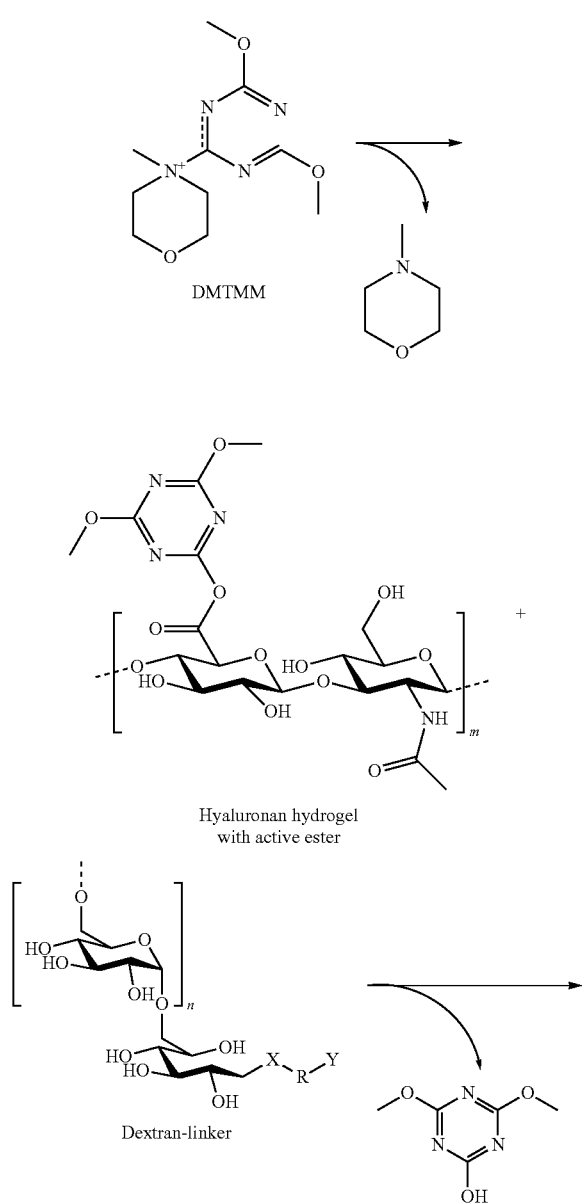

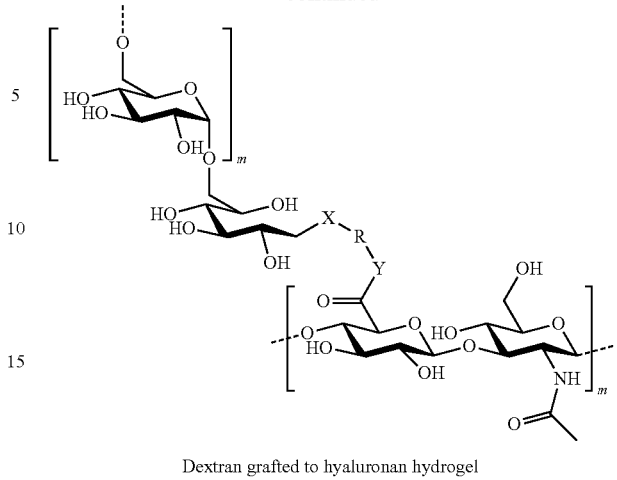

Dextran grafted to hyaluronan hydrogel

The carboxylic group of the cross-linked hyaluronic acid reacts with the activating agent to form an active ester. The functional group Y is a functional group capable of reacting with the active ester. The functional group Y may for example be amine, hydrazide, carbazate, semicarbazide, thiosemicarbazide, thiocarbazate or aminooxy. The activating agent is a suitable coupling agent (e.g. a carbodiimide coupling agent together with activator such as a hydroxylamine derivative, or a triazine). The functional group Y reacts with the active ester to graft the dextran to the cross-linked hyaluronic acid. Suitable reaction conditions for grafting the functionalized dextran (dextran-linker) to the cross-linked hyaluronic acid include pH in the range of 3-12, reaction time in the range of 1-48 h, reaction temperature in the range of 15-70° C., molar ratio of coupling agent to hyaluronic acid carboxyl groups in the range of 0.1:1 to 10:1, molar ratio of dextran-linker to hyaluronic acid carboxyl groups in the range of 0.05:1 to 5:1 and a concentration of cross-linked hyaluronic acid in the range of 1-50 mg/mL.

According to some embodiments of the process, the grafting of step (b) involves:
(i) activating the carboxyl groups on the cross-linked hyaluronic acid with a coupling agent to form an activated cross-linked hyaluronic acid; and
(ii) coupling the linker of the one or more functionalized dextran molecules to the carboxyl groups of the activated cross-linked hyaluronic acid.

According to some embodiments, the activation of the cross-linked hyaluronic acid and the coupling of the dextran molecule to the activated cross-linked hyaluronic acid occur simultaneously in step (b).

According to some embodiments, the activation of the cross-linked hyaluronic acid occurs prior to and separately from the coupling of the dextran molecule to the activated cross-linked hyaluronic acid in step (b).

According to some embodiments, the coupling agent is selected from the group consisting of triazine-based coupling agents, carbodiimide coupling agents, imidazolium-derived coupling agents, Oxyma and COMU. According to some embodiments, the coupling agent is a triazine-based coupling agent. According to some embodiments, the triazine-based coupling agent is selected from the group consisting of 4-(4,6-dimethoxy-1,3,5-triazin-2-yl)-4-methyl-morpholinium chloride (DMTMM) and 2-chloro-4,6- dimethoxy-1,3,5-triazine (CDMT). In a preferred embodiment, the triazine-based coupling agent is DMTMM.

Further preferred embodiments of steps (a) and (b) are evident from the description above relating to the resulting hyaluronic acid product. In particular, step (b) may further comprise size reduction of the cross-linked hyaluronic acid into particles, strings, discs, etc.

Since the nature of the product obtainable by the processes according to the invention is complex, the product may also be defined as being the result of these processes.

The inventors have surprisingly found that it is possible to graft dextran directly to a cross-linked hyaluronic acid gel with high conversion. Grafting is preferably performed by covalent single end-point attachment of the dextran to the hyaluronic acid via a suitable linker. Hyaluronic acid products according to the present invention, comprising a cross-linked hyaluronic acid and one or more dextran molecules, display several advantageous and surprising properties.

The swelling capacity and thereby the ability to absorb water was surprisingly reduced by grafting dextran to carboxylic groups of the hyaluronic acid gel. This reduction in swelling capacity is shown in FIG. 1. The reduced swelling is useful, since it means that harder gels can be produced, without increasing the amount of cross-linker in the hyaluronic acid.

Figure 2:
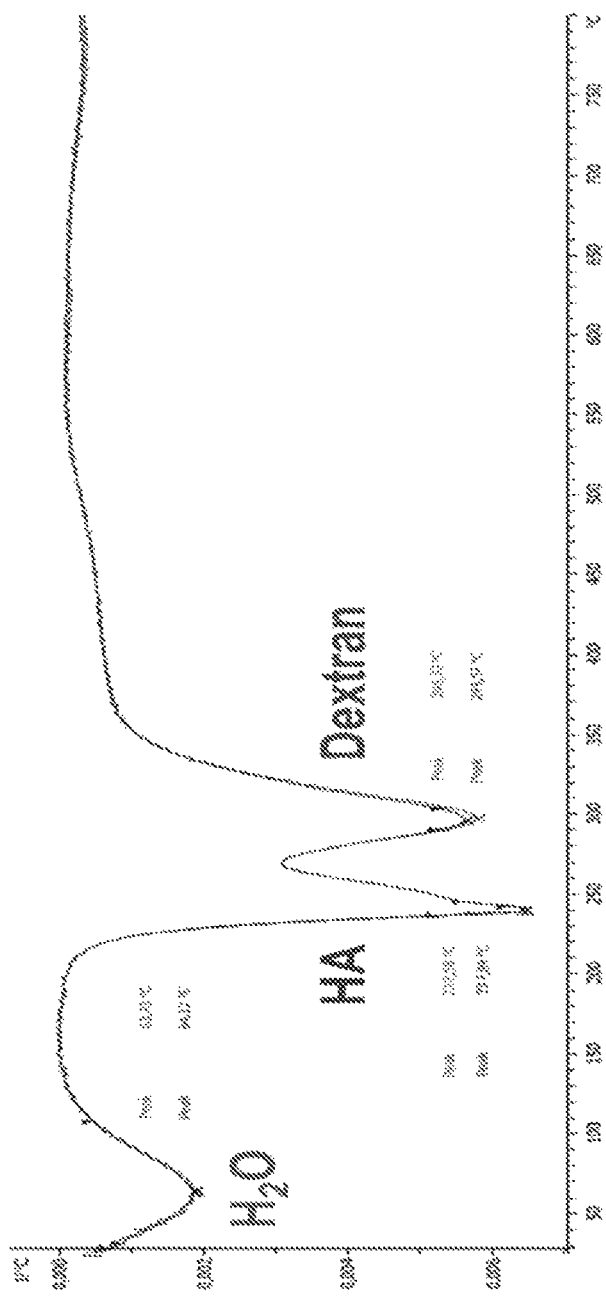
FIG. 2 Thermal gravimetric analysis of a HA-dextran mixed hydrogel.

The dextran grafts are expected to protect the hydrogel backbone from heat degradation as dextran is more stable to degradation than hyaluronic acid. The thermal stability of dextran has been shown to be much higher than that of hyaluronic acid based on results from thermal gravimetric analysis of a mixed hydrogel of hyaluronic acid and dextran (FIG. 2).

The dextran grafts to protect the cross-linked hyaluronic acid from enzymatic degradation by, for instance, chondroitinase and hyaluronidase, due to steric hindrance and/or a reduced number of available carboxylic groups (essential for enzymatic function).

The dextran grafts are expected to protect the hydrogel backbone from hydrolysis as the 1-6 glycosidic bond in dextran is more resistant than the 1-3 and 1-4 glycosidic bonds in hyaluronic acid.

The synthetic protocols employed to graft dextran to hyaluronic acid by amide bonds involve mild and neutral conditions, and unwanted degradation of the hyaluronan backbone is therefore avoided.

Figure 3:
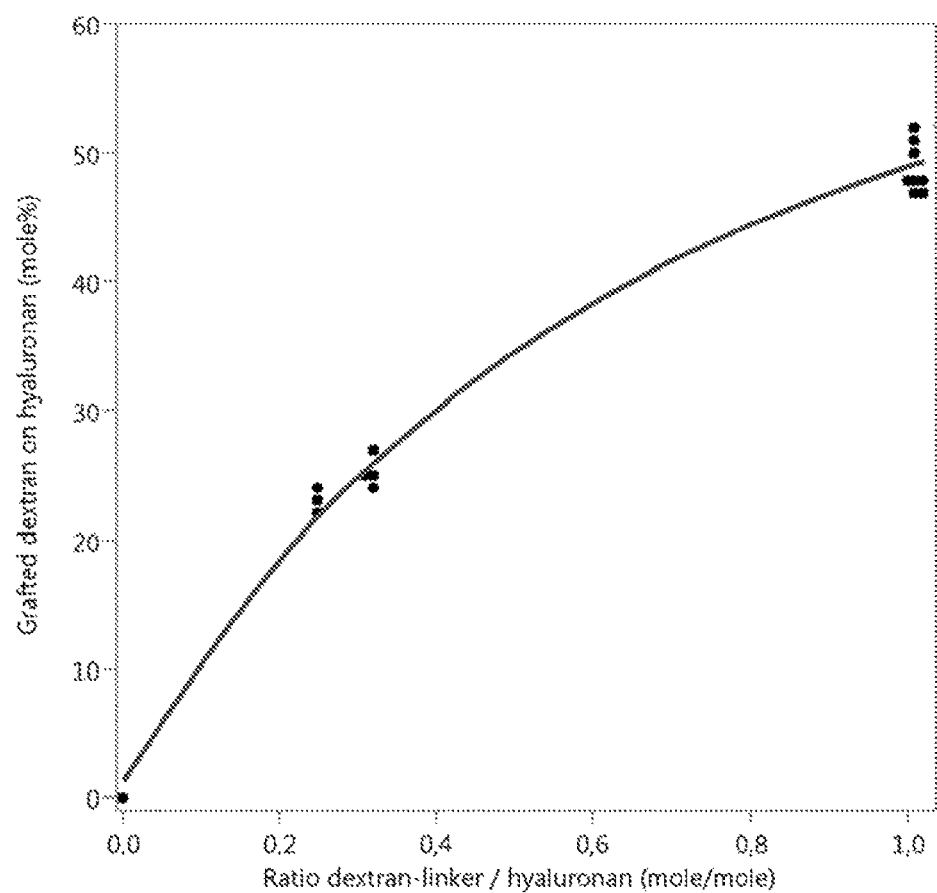
FIG. 3 Grafted dextran on HA as a function of dextran-linker/HA ratio.

The processes according to the invention also enable highly controllable grafting ratios, degrees of substitution or modification of the HA network by varying the amount of functionalized dextran added (FIG. 3).

The dextran grafts are believed to protect the hydrogel backbone from radical degradation as dextran may react with radicals more preferably than the HA hydrogel network. The dextran, which is attached to the HA hydrogel by a single end-point attachment, will also be more available to radicals.

Finally, the grafting is highly chemoselective and regiospecific as the bifunctional linker only reacts with the reducing end of dextran by a single-point attachment, and the carboxylic acid of hyaluronan in the HA hydrogel network, resulting in highly defined structures.

Without desiring to be limited thereto, the present invention will in the following be illustrated by way of examples.

EXAMPLES

Characterization

Reductive Amination on Dextran

The modification of dextran with a linker was analyzed with $^1$H NMR and LC-QToF-MS.

Grafting of Dextran to Hyaluronan Gel

The hydrogels were degraded with chondroitinase ABC or HCl prior to the analysis. The amount of grafted dextran on hyaluronan was analyzed with $^1$H NMR spectroscopy.

LC-QToF-MS analysis was made to confirm the link between dextran—linker—hyaluronan, but only if the material could be degraded with enzymes.

Swelling was done in saline.

Example 1—Reductive Amination of Dextran

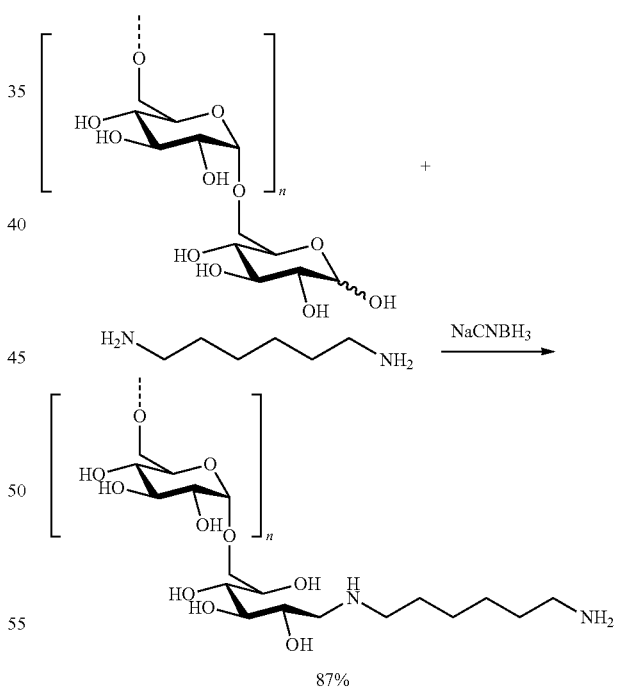

50.0 g dextran with a number average molecular weight ($M_n$) of 750 Da, 118.4 g hexamethylenediamine dihydrochloride and 39.4 g NaCNBH$_3$ were weighed in a 500 mL glass bottle. The reagents were dissolved in 250 g 50 mM sodium tetraborate buffer. The pH was adjusted to pH 9.8 with 1 M NaOH. The bottle was placed in a water bath at 60° C. for 3 h.

The reaction crude was neutralized to pH 7 with diluted HCl and was transferred to a 3 L plastic beaker. The reaction crude was precipitated while stirring with an over-head stirrer and slowly adding ethanol using a peristaltic pump up to final ethanol concentration of 90%. The precipitate was washed with 90% ethanol numerous times to completely remove non-bonded reaction chemicals and dried in a vacuum dryer.

The dry powder was dissolved in $D_2O$ and analyzed by $^1H$ NMR. It was found by that 87% of the total dextran in the sample was coupled to hexamethylenediamine by comparing the signals from the anomeric proton of dextran (4.94 ppm) to the hexamethylenediamine signal (1.33 ppm).

Example 2—Reductive Amination of Maltotriose

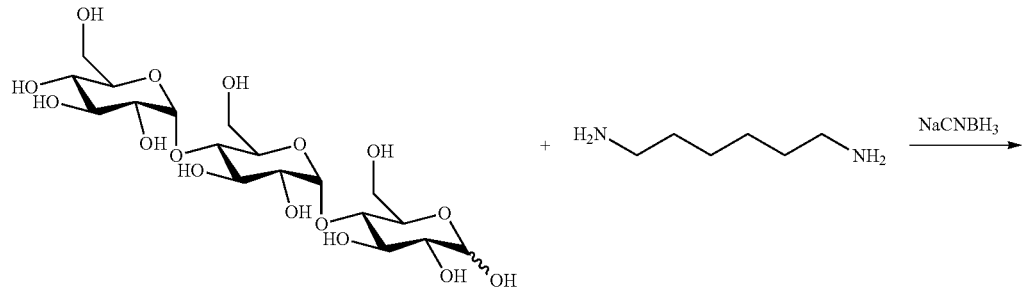

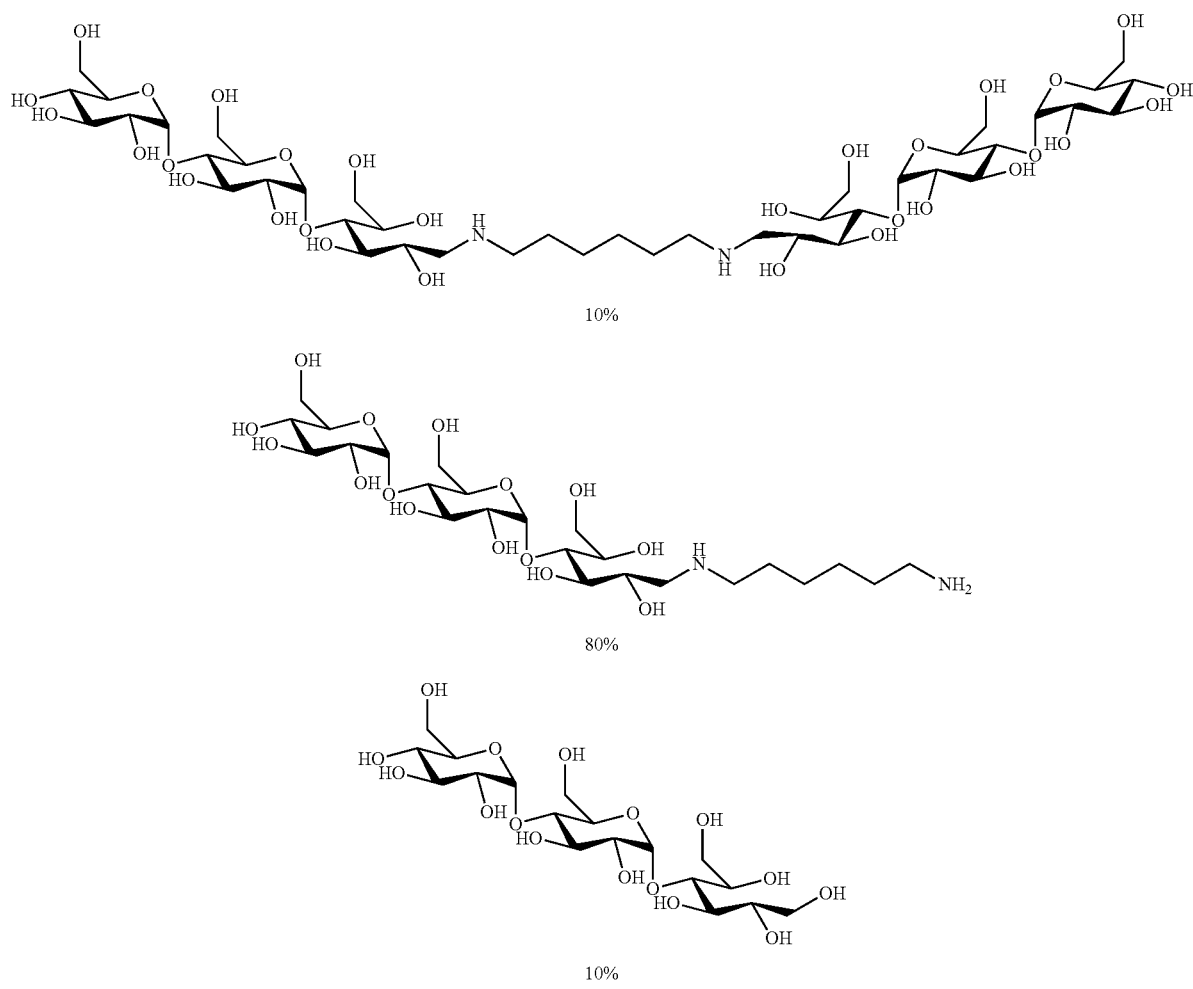

1.0 g maltotriose, 1.9 g hexamethylenediamine dihydrochloride and 0.7 g NaCNBH$_3$ were weighed in a 20 mL glass vial with an aluminum lid. The reagents were dissolved in 5 g 50 mM sodium tetraborate buffer. The pH was adjusted to 10 with 1 M NaOH. The vial was then placed in a water bath at 60° C. for 3 h.

The reaction crude was neutralized to pH 7 with diluted HCl. The crude was analyzed after dilution on LC-QToF-MS using negative electrospray. It was found that the solution was composed of 80 area % maltotriose-NMDA (m/z 603.30), 10 area % maltotriose-HMDA-maltotriose (m/z 1091.47) and 10 area % reduced malotriose (m/z 505.18).

Example 3—Reductive Amination of Dextran

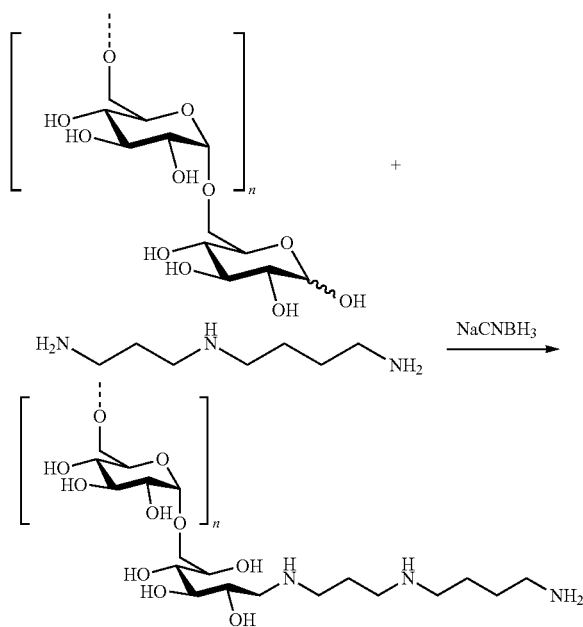

5.0 g dextran with M$_n$ 1100 Da 5.4 g spermidine trihydrochloride and 1.6 g NaCNBH$_3$ were weighed in a 50 mL glass bottle. The reagents were dissolved in 14.3 g 50 mM sodium tetraborate buffer. The pH was adjusted to pH 9.3 with 1 M NaOH. The bottle was placed in a water bath at 60° C. for 2 h.

The reaction crude was neutralized to pH 7 with diluted HCl and was transferred to a 3 L plastic beaker. The reaction crude was precipitated while stirring with an over-head stirrer and slowly adding ethanol using a peristaltic pump up to final ethanol concentration of 90%. The precipitate was washed with 90% ethanol numerous times to completely remove non-bonded reaction chemicals and dried in a vacuum dryer.

The dry powder was dissolved in D$_2$O and analyzed by $^1$H NMR. It was confirmed that dextran was modified with spermidine when the signal from anomeric protons of dextran (4.94 ppm) was compared to the spermidine signal (1.76 ppm).

Example 4—Reductive Amination of Dextran

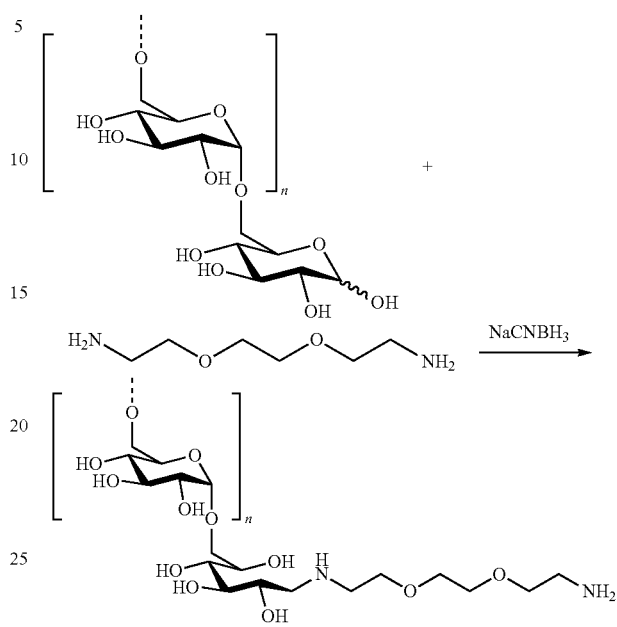

5.0 g dextran with M$_n$ 1100 Da, 3.4 g 2,2'-(ethylenedioxy)bis(ethylamine) and 1.5 g NaCNBH$_3$ were weighed in a 50 mL glass bottle. The reagents were dissolved in 15.0 g 50 mM sodium tetraborate buffer. The pH was adjusted to 10.3 with 1 M NaOH. The bottle was placed in a water bath at 60° C. for 2 h.

The reaction crude was neutralized to pH 7 with diluted HCl and was transferred to a 3 L plastic beaker. The reaction crude was precipitated while stirring with an over-head stirrer and slowly adding ethanol using a peristaltic pump up to final ethanol concentration of 90%. The precipitate was washed with 90% ethanol numerous times to completely remove non-bonded reaction chemicals and dried in a vacuum dryer.

The dry powder was dissolved in D$_2$O and analyzed by $^1$H NMR. It was confirmed that dextran was modified with 2,2'-(ethylenedioxy)bis(ethylamine) when the signal from the anomeric protons of dextran (4.94 ppm) was compared to the 2,2'-(ethylenedioxy)bis(ethylamine) signal (3.20 ppm).

Example 5—Reductive Amination of Dextran

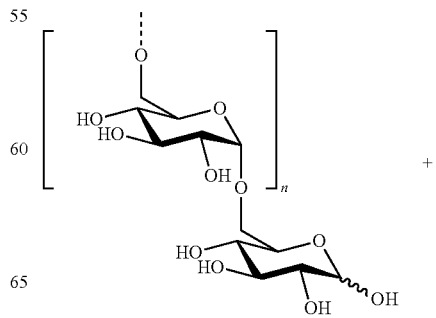

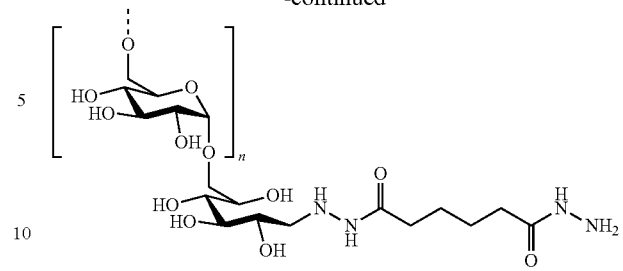

5.1 g dextran with $M_n$ 1100 Da, 4.1 g O,O'-1,3-propanediylbishydroxylamine dihydrochloride and 1.5 g NaCNBH$_3$ were weighed in a 50 mL glass bottle. The reagents were dissolved in 13.4 g 50 mM sodium tetraborate buffer. The pH was adjusted to 9.7 with 1 M NaOH. The bottle was placed in a water bath at 60° C. for 2 h.

The reaction crude was neutralized to pH 7 with diluted HCl and was transferred to a 3 L plastic beaker. The reaction crude was precipitated while stirring with an over-head stirrer and slowly adding ethanol using a peristaltic pump up to final ethanol concentration of 90%. The precipitate was washed with 90% ethanol numerous times to completely remove non-bonded reaction chemicals and dried in a vacuum dryer.

The dry powder was dissolved in D$_2$O and analyzed by $^1$H NMR. It was confirmed that dextran was modified with O,O'-1,3-Propanediylbishydroxylamine when the signal from the anomeric protons of dextran (4.94 ppm) was compared compared to the O,O'-1,3-Propanediylbishydroxylamine signal (4.18 ppm).

Example 6—Reductive Amination of Dextran

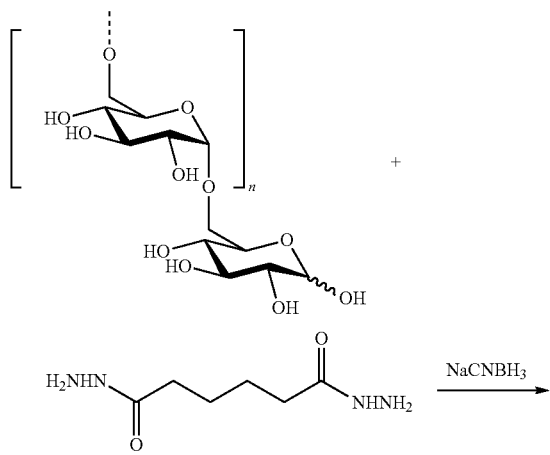

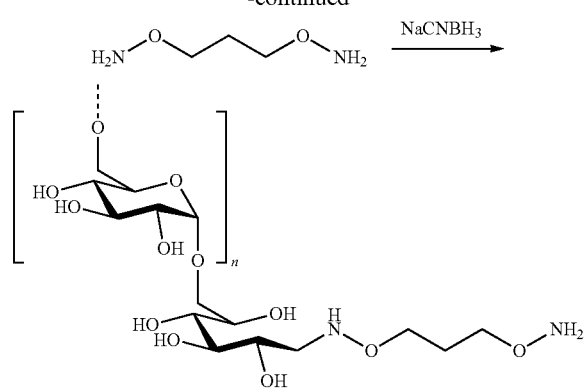

5.0 g dextran with $M_n$ 1100 Da, 4.1 g adipic acid dihydrazide and 1.7 g NaCNBH$_3$ were weighed in a 50 mL glass bottle. The reagents were dissolved in 13.5 g 50 mM sodium tetraborate buffer. The pH was adjusted to 9.5 with 1 M NaOH. The bottle was placed in a water bath at 60° C. for 2 h.

The reaction crude was neutralized to pH 7 with diluted HCl and was transferred to a 3 L plastic beaker. The reaction crude was precipitated while stirring with an over-head stirrer and slowly adding ethanol using a peristaltic pump up to final ethanol concentration of 90%. The precipitate was washed with 90% ethanol numerous times to completely remove non-bonded reaction chemicals and dried in a vacuum dryer.

The dry powder was dissolved in D$_2$O and analyzed by $^1$H NMR. It was confirmed that dextran was modified with adipic acid dihydrazide when the signal from the anomeric protons of dextran (4.94 ppm) was compared to the adipic acid dihydrazide signal (1.60 ppm).

Examples 7 to 13—Grafting of Functionalized Dextran to a Hyaluronan Gel

In examples 7-13, functionalized dextran molecules were grafted to a hyaluronic acid hydrogel. The hyaluronic acid gel was prepared according to the general procedure described in Examples 1 and 2 of international patent application WO 97/04012 (Ågerup et al.).

The term conversion in used in Examples 7-13 is defined as moles of grafted modified dextran divided by total moles modified dextran used in the reaction.

Example 7—Grafting Dextran (1 kDa) with Hexamethylenediamine to Hydrogel

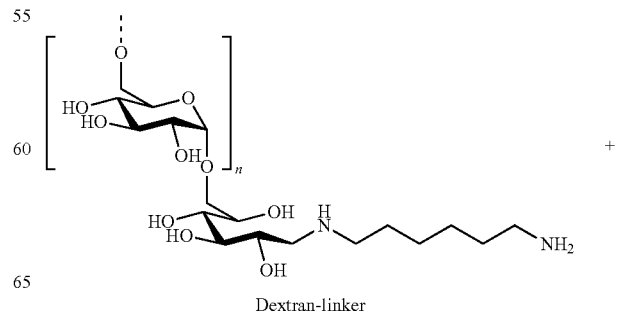

Dextran-linker

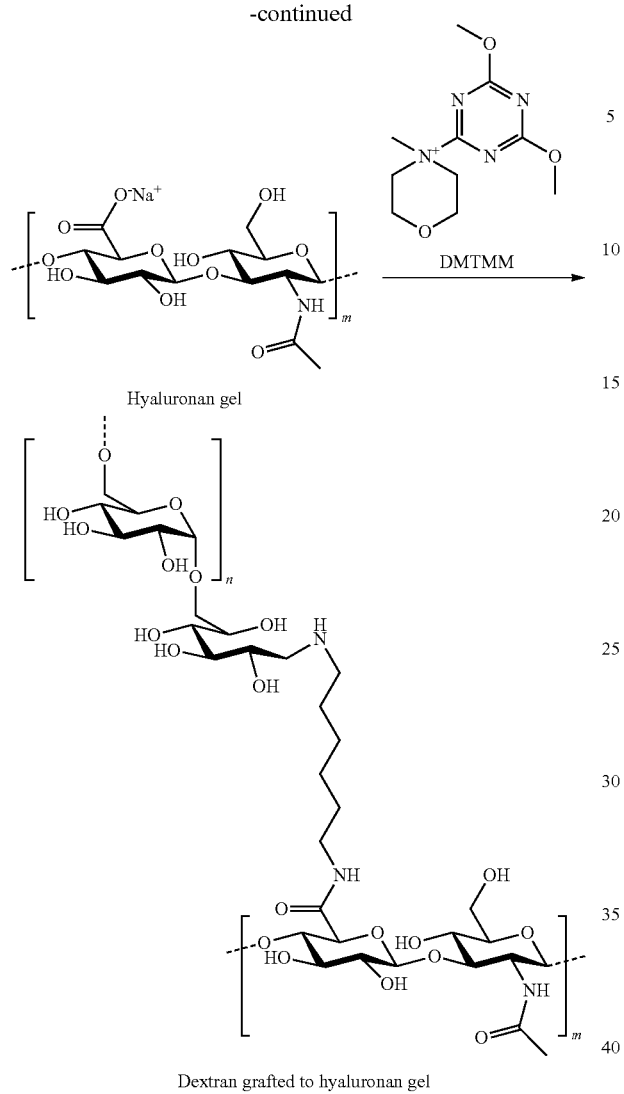

Hyaluronan gel

Dextran grafted to hyaluronan gel 1.1 g dextran 1 kDa modified at the reducing end with hexamethylenediamine and 5.6 g DMTMM were weighed in a 100 mL glass bottle. 80 g 1 mM phosphate buffer pH 7.4 was added to dissolve the reagents. 1.6 g precipitated hyaluronan hydrogel was added to the reaction solution while stirring so that a concentration of 20 mg/mL hyaluronan was obtained. The sample was placed in a water bath 50° C. and allowed to react for a day.

The hydrogel was particle size reduced and washed on a 0.2 μm filter with 0.9% NaCl one time. The pH was increased to 13 with 0.25 M NaOH. The hydrogel was neutralized after 90 min with diluted HCl to neutral pH. The gel was continuously washed with 0.9% NaCl and then precipitated by stirring it with an over-head stirrer and slowly adding ethanol with a peristaltic pump up to 70% ethanol. The precipitate was washed with 70% ethanol numerous times. The precipitated hydrogel was then dried in a vacuum dryer.

$^1$H NMR shows a degree of modification (mole of dextran chains/mole of HA disaccharide repeating units) of 27% by comparing the anomeric protons of dextran (4.94 ppm) with the N-acetyl protons of HA (2.02 ppm). The conversion of the dextran in the reaction was 85%. The coupling dextran—linker—HA was confirmed with LC-QToF-MS. The initial swelling factor of the gel was 1.6 mL/g and after the reaction it had decreased to 0.9 mL/g.

Example 8—Grafting Dextran (1 kDa) with Hexamethylenediamine to Hydrogel

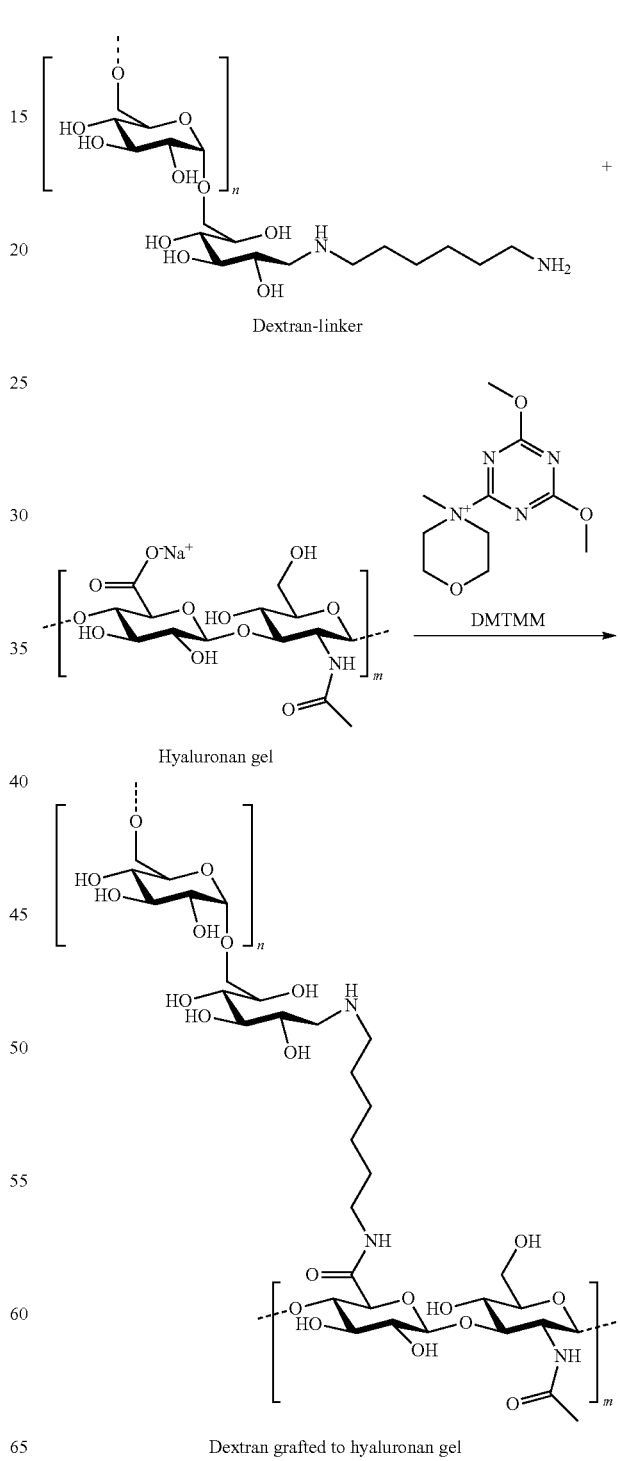

Dextran-linker

Hyaluronan gel

Dextran grafted to hyaluronan gel 3.5 g dextran 1 kDa modified at the reducing end with hexamethylenediamine and 5.6 g DMTMM were weighed in a 100 mL glass bottle. 80 g 1 mM phosphate buffer pH 7.4 was added to dissolve the reagents. 1.6 g precipitated hyaluronan hydrogel was added to the reaction solution while stirring so that a concentration of 20 mg/mL hyaluronan was obtained. The sample was placed in a water bath 50° C. and allowed to react for a day.

The hydrogel was particle size reduced and washed on a 0.2 μm filter with 0.9% NaCl one time. The pH was increased to 13 with 0.25 M NaOH. The hydrogel was neutralized after 90 min with diluted HCl to neutral pH. The gel was continuously washed with 0.9% NaCl and then precipitated by stirring it with an over-head stirrer and slowly adding ethanol with a peristaltic pump up to 70% ethanol. The precipitate was washed with 70% ethanol a couple of times. The precipitated hydrogel was then dried in a vacuum dryer.

$^1$H NMR shows a degree of modification (mole of dextran chains/mole of HA disaccharide repeating units) of 47% by comparing the anomeric protons of dextran (4.94 ppm) with the N-acetyl protons of HA (2.02 ppm). The conversion of the dextran in the reaction was 46%. The coupling dextran—linker—HA was confirmed with LC-QToF-MS. The initial swelling factor of the gel was 5.1 mL/g and after the reaction it had decreased to 2.7 mL/g.

Example 9—Grafting Dextran (1 kDa) with Spermidine to Hydrogel

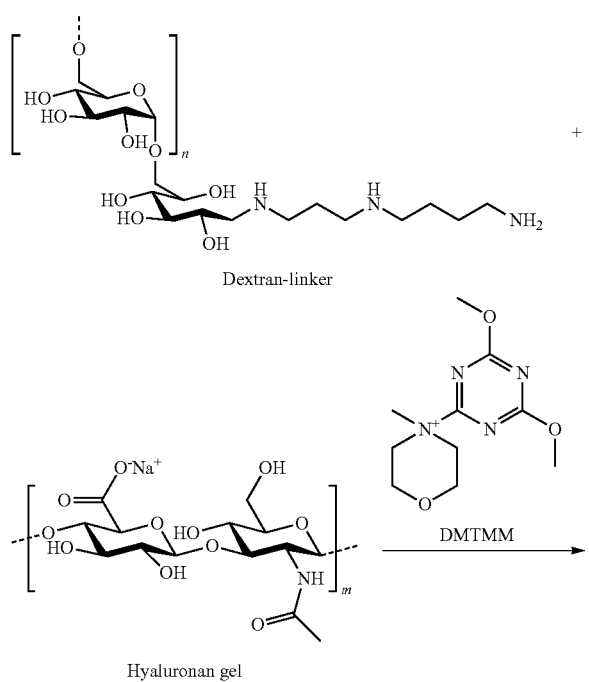

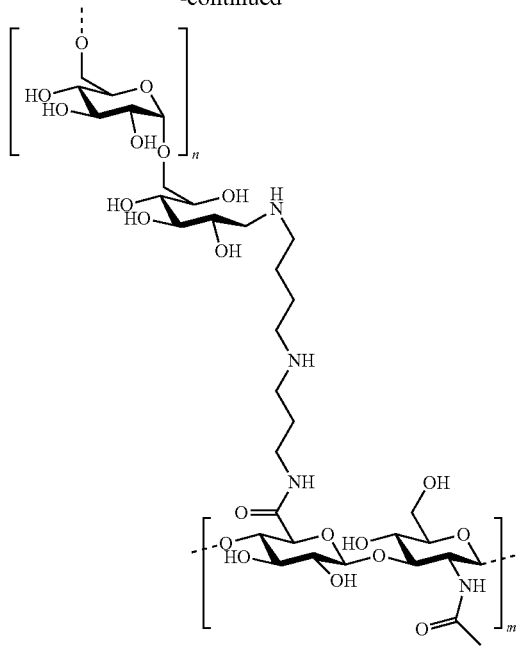

Dextran grafted to hyaluronan gel 0.5 g dextran 1 kDa modified at the reducing end with spermidine and 0.6 g DMTMM were weighed in a 50 mL plastic bottle. 20 g 1 mM phosphate buffer pH 7.4 was added to dissolve the reagents. The pH of the solution adjusted to be 7.0 with diluted HCl. 0.4 g precipitated hyaluronan hydrogel was added to the reaction solution while stirring so that a concentration of 20 mg/mL hyaluronan was obtained. The sample was placed in a water bath 50° C. and allowed to react for a day.

The hydrogel was particle size reduced and washed on a 0.2 μm filter with 0.9% NaCl one time. The pH was increased to 13 with 0.25 M NaOH. The hydrogel was neutralized after 70 min with diluted HCl to neutral pH. The gel was transferred to a column coupled to a peristaltic pump. The hydrogel was continuously washed by pumping 2.5 L 0.9% NaCl from the bottom to the top. The gel was then removed from the column and analyzed.

$^1$H NMR shows a degree of modification (mole of dextran chains/mole of HA disaccharide repeating units) of 18% by comparing the anomeric protons of dextran (4.94 ppm) with the N-acetyl protons of HA (2.02 ppm). The conversion of the dextran in the reaction was 78%. The coupling dextran—linker—HA could not be confirmed with LC-QToF-MS since the material was not fully degraded with chondroitinase ABC.

Example 10—Grafting Dextran (1 kDa) with 2,2'-(Ethylenedioxy)bis(ethyl-amine) to Hydrogel

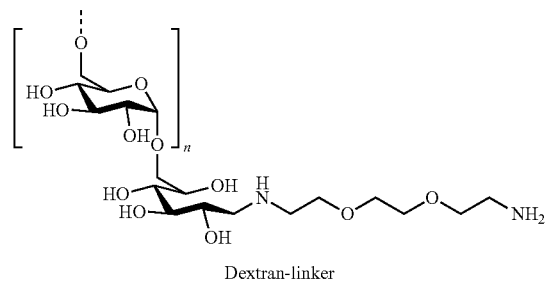

Dextran-linker

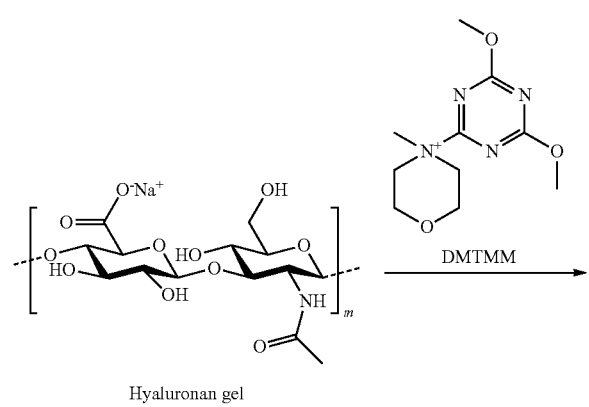

Hyaluronan gel

Dextran grafted to hyaluronan ogel 0.5 g dextran 1 kDa modified at the reducing end with 2,2'-(Ethylenedioxy)bis(ethylamine) and 0.6 g DMTMM were weighed in a 50 mL plastic bottle. 20 g 1 mM phosphate buffer pH 7.4 was added to dissolve the reagents. The pH of the solution adjusted to be 7.1 with diluted HCl. 0.4 g precipitated hyaluronan hydrogel was added to the reaction solution while stirring so that a concentration of 20 mg/mL hyaluronan was obtained. The sample was placed in a water bath 50° C. and allowed to react for a day.

The hydrogel was particle size reduced and washed on a 0.2 μm filter with 0.9% NaCl one time. The pH was increased to 13 with 0.25 M NaOH. The hydrogel was neutralized after 70 min with diluted HCl to neutral pH. The hydrogel was transferred to a column coupled to a peristaltic pump. The gel was continuously washed by pumping 2.5 L 0.9% NaCl from the bottom to the top. The gel was then removed from the column and analyzed.

$^1$H NMR shows a degree of modification (mole of dextran chains/mole of HA disaccharide repeating units) of 21% by comparing the anomeric protons of dextran (4.94 ppm) with the N-acetyl protons of HA (2.02 ppm). The conversion of the dextran in the reaction was 90%. The coupling dextran—linker—HA was confirmed with LC-QToF-MS.

Example 11—Grafting Dextran (1 kDa) with O,O'-1,3-Propanediylbis-Hydroxylamine to Hydrogel

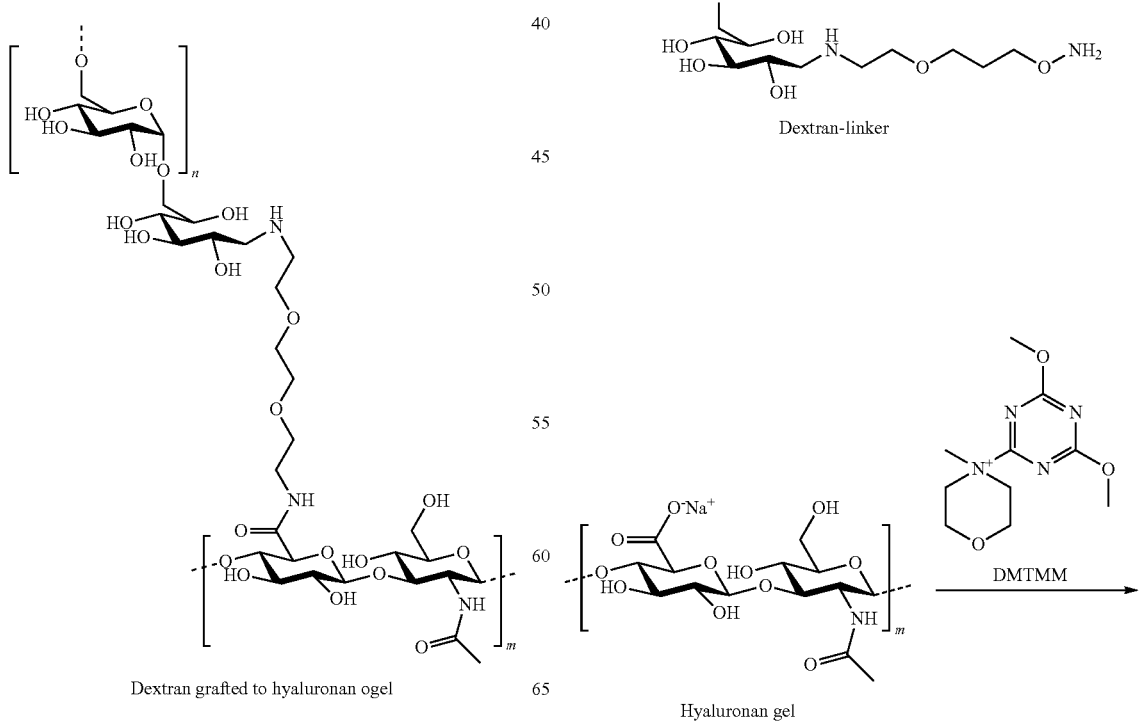

-continued

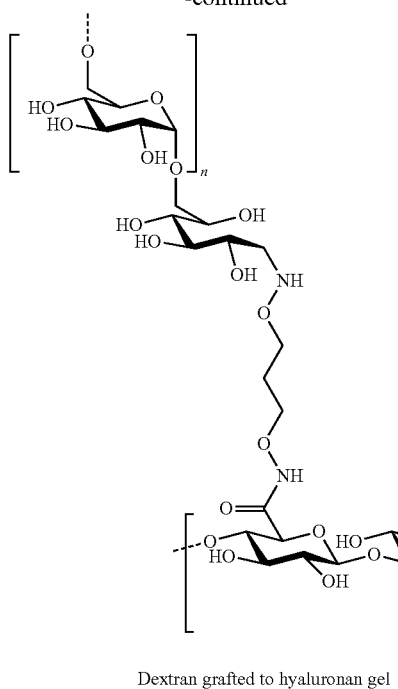

Dextran grafted to hyaluronan gel 0.5 g dextran 1 kDa modified at the reducing end with O,O'-1,3-Propanediylbishydroxylamine and 0.6 g DMTMM were weighed in a 50 mL plastic bottle. 20 g 1 mM phosphate buffer pH 7.4 was added to dissolve the reagents. The pH of the solution adjusted to be 6.9 with diluted HCl. 0.4 g precipitated hyaluronan hydrogel was added to the reaction solution while stirring so that a concentration of 20 mg/mL hyaluronan was obtained. The sample was placed in a water bath 50° C. and allowed to react for a day.

The hydrogel was particle size reduced and washed on a 0.2 μm filter with 0.9% NaCl one time. The pH was increased to 13 with 0.25 M NaOH. The hydrogel was neutralized after 75 min with diluted HCl to neutral pH. The hydrogel was transferred to a column coupled to a peristaltic pump. The gel was continuously washed by pumping 2.5 L 0.9% NaCl from the bottom to the top. The gel was then removed from the column and analyzed.

$^1$H NMR shows a degree of modification (mole of dextran chains/mole of HA disaccharide repeating units) of 11% by comparing the anomeric protons of dextran (4.94 ppm) with the N-acetyl protons of HA (2.02 ppm). The conversion of the dextran in the reaction was 49%. The coupling dextran—linker—HA was confirmed with LC-QToF-MS.

Example 12—Grafting Dextran (1 kDa) with Adipic Acid Dihydrazide to Hydrogel

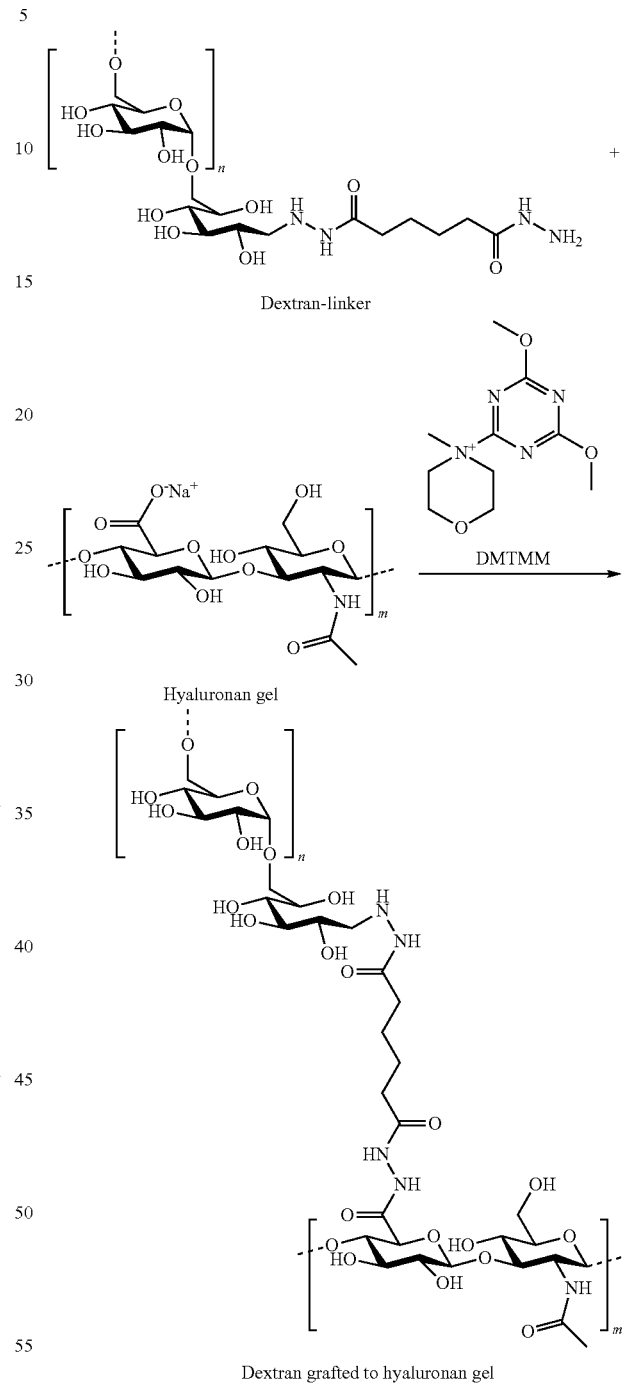

0.5 g dextran 1 kDa modified at the reducing end with adipic acid dihydrazide and 0.6 g DMTMM were weighed in a 50 mL plastic bottle. 20 g 1 mM phosphate buffer pH 7.4 was added to dissolve the reagents. The pH of the solution adjusted to be 7.1 with diluted HCl. 0.4 g precipitated hyaluronan hydrogel was added to the reaction solution while stirring so that a concentration of 20 mg/mL hyaluronan was obtained. The sample was placed in a water bath 50° C. and allowed to react for a day.

The hydrogel was particle size reduced and washed on a 0.2 μm filter with 0.9% NaCl one time. The pH was increased to 13 with 0.25 M NaOH. The hydrogel was neutralized after 75 min with diluted HCl to neutral pH. The hydrogel was transferred to a column coupled to a peristaltic pump. The gel was continuously washed by pumping 2.5 L 0.9% NaCl from the bottom to the top. The gel was then removed from the column and analyzed.

$^1$H NMR shows a degree of modification (mole of dextran chains/mole of HA disaccharide repeating units) of 5% by comparing the anomeric protons of dextran (4.94 ppm) with the N-acetyl protons of HA (2.02 ppm). The conversion of the dextran in the reaction was 20%. The coupling dextran—linker—HA could not be confirmed with LC-QToF-MS since the material was not fully degraded with chondroitinase ABC.

Example 13—Grafting Maltotriose with Hexamethylenediamine to Hydrogel

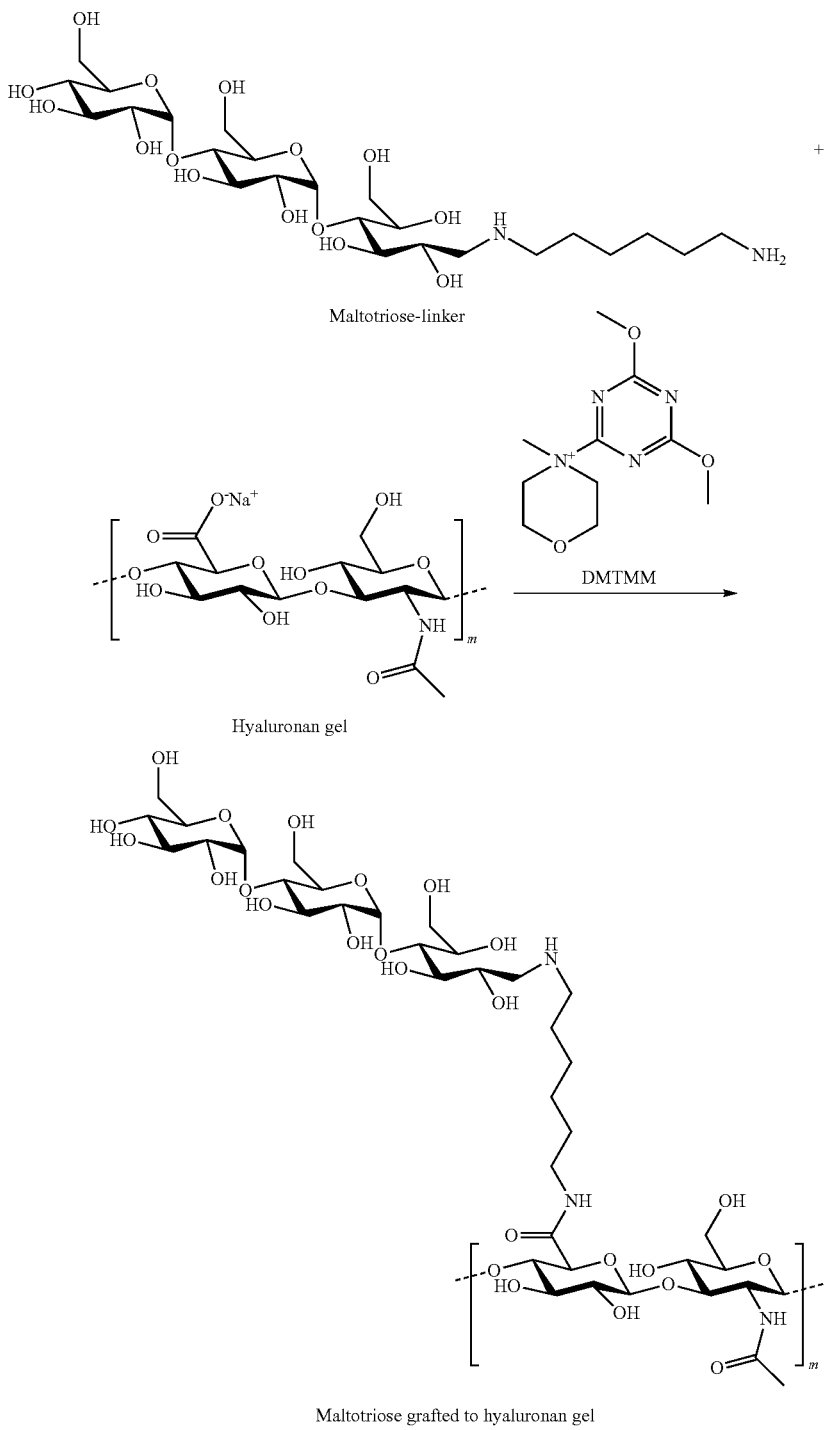

Maltotriose-linker

Hyaluronan gel

Maltotriose grafted to hyaluronan gel 0.3 g maltotriose modified at the reducing end with hexamethylenediamine and 0.6 g DMTMM were weighed in a 50 mL plastic bottle. 20 g 1 mM phosphate buffer pH 7.4 was added to dissolve the reagents. The pH of the solution adjusted to 7.0 with diluted HCl. 0.4 g precipitated hyaluronan hydrogel was added to the reaction solution while stirring so that a concentration of 20 mg/mL hyaluronan was obtained. The sample was placed in a water bath 50° C. and allowed to react for a day.

The hydrogel was particle size reduced and washed on a 0.2 µm filter with 0.9% NaCl one time. The pH was increased to 13 with 0.25 M NaOH. The hydrogel was neutralized after 80 min with diluted HCl to neutral pH. The hydrogel was transferred to a column coupled to a peristaltic pump. The gel was continuously washed by pumping 2.5 L 0.9% NaCl from the bottom to the top. The gel was then removed from the column and analyzed.

$^1$H NMR shows a degree of modification (mole of maltotriose chains/mole of HA disaccharide repeating units) of 10% by comparing the anomeric protons of maltotriose (4.94 ppm) with the N-acetyl protons of HA (2.02 ppm). The conversion of the maltotriose in the reaction was 43%. The coupling maltotriose—linker—HA was confirmed with LC-QToF-MS.

The invention claimed is:

1. A hyaluronic acid product comprising a cross-linked hyaluronic acid and one or more dextran molecules, wherein the hyaluronic acid is cross-linked by ether bonds and the one or more dextran molecules are covalently grafted to the cross-linked hyaluronic acid, wherein the dextran molecules are covalently linked to the hyaluronic acid by single end-point attachment via a bi- or polyfunctional linker between the reducing end of dextran and a carboxyl group of hyaluronic acid.

2. A hyaluronic acid product according to claim 1, wherein the cross-linked hyaluronic acid is in the form of a gel.

3. A hyaluronic acid product according to claim 1, wherein the cross-linked hyaluronic acid is in the form of gel particles having an average size in the range of 0.01-5 mm.

4. A hyaluronic acid product according to claim 1, wherein the hyaluronic acid chains are cross-linked to each other via a linker which is derived from a bi- or polyfunctional cross-linking agent.

5. A hyaluronic acid product according to claim 4, wherein said bi- or polyfunctional cross-linking agent is a bis- or polyepoxide.

6. A hyaluronic acid product according to claim 5, wherein said bi- or polyfunctional cross-linking agent is a diglycidyl ether.

7. A hyaluronic acid product according to claim 6, wherein said bi- or polyfunctional cross-linking agent is selected from the group consisting of 1,4-butanediol diglycidyl ether (BDDE), 1,2-bis(2,3-epoxypropoxy)ethylene (EGDGE) and ethylene glycol diglycidyl ether (EGDE), 1,2-ethanediol diglycidyl ether (EDDE) and diepoxyoctane.

8. A hyaluronic acid product according to claim 7, wherein said bi- or polyfunctional cross-linking agent is 1,4-butanediol diglycidyl ether (BDDE).

9. A hyaluronic acid product according to claim 1, wherein the one or more dextran molecules and the disaccharides of the cross-linked hyaluronic acid have a molar ratio of 0.1-99%.

10. A hyaluronic acid product according to claim 1, wherein the one or more dextran molecules and the disaccharides of the cross-linked hyaluronic acid have a molar ratio of 1-60%.

11. A hyaluronic acid product according to claim 1, wherein the dextran molecules have an average molecular weight of less than 10 kDa.

12. A hyaluronic acid product according to claim 1, wherein the dextran molecules have an average molecular weight of less than 5 kDa.

13. A hyaluronic acid product according to claim 1, wherein the dextran molecule contains a linker having an amino, hydrazide, carbazate, semicarbazide, thiosemicarbazide, thiocarbazate or aminooxy functional group, and wherein the functional group of the linker forms a covalent bond with a carboxyl group of the cross-linked hyaluronic acid.

14. A hyaluronic acid product according to claim 13, wherein the bi- or polyfunctional linker comprises a diamine or a dihydrazide.

15. A hyaluronic acid product according to claim 1, wherein the one or more dextran molecules are covalently grafted to the cross-linked hyaluronic acid by amide bonds.

16. A process of preparing a hyaluronic acid product comprising a cross-linked hyaluronic acid and one or more dextran molecules, the process comprising the steps of:
    (a) providing a cross-linked hyaluronic acid and one or more functionalized dextran molecules;
    (b) covalently grafting one or more functionalized dextran molecules to the cross-linked hyaluronic acid;
    wherein the functionalized dextran molecules provided in step (a) are functionalized at the reducing end with a bi- or polyfunctional linker having at least one functional group available for linking the dextran molecules to a carboxyl group of the cross-linked hyaluronic acid.

17. A process according to claim 16, wherein the cross-linked hyaluronic acid in step (a) is in the form of a gel.

18. A process according to claim 16, wherein the cross-linked hyaluronic acid in step (a) is in the form of gel particles having an average size in the range of 0.01-5 mm.

19. A process according to claim 16, wherein the one or more dextran molecules and the disaccharides of the cross-linked hyaluronic acid of the resulting hyaluronic acid product have a molar ratio of 0.1-99%.

20. A process according to claim 16, wherein the one or more dextran molecules and the disaccharides of the cross-linked hyaluronic acid of the resulting hyaluronic acid product have a molar ratio of 1-60%.

21. A process according to claim 16, wherein the dextran molecules provided in step (a) have an average molecular weight of less than 10 kDa.

22. A process according to claim 16, wherein the dextran molecules provided in step (a) have an average molecular weight of less than 5 kDa.

23. A process according to claim 16, wherein the one or more functionalized dextran molecules of step (a) contain a linker having an amino, hydrazide, carbazate, semicarbazide, thiosemicarbazide, thiocarbazate or aminooxy functional group, and wherein the functional group of the linker forms a covalent bond with a carboxyl group of the cross-linked hyaluronic acid.

24. A process according to claim 23, wherein the bi- or polyfunctional linker comprises a diamine or a dihydrazide.

25. A process according to claim 16, wherein the covalent grafting of step (b) involves:
    (i) activating the carboxyl groups on the cross-linked hyaluronic acid with a coupling agent to form an activated cross-linked hyaluronic acid; and
    (ii) coupling the linker of the one or more functionalized dextran molecules to the carboxyl groups of the activated cross-linked hyaluronic acid.

26. A process according to claim 25, wherein the activation of the cross-linked hyaluronic acid and the coupling of the dextran molecule to the activated cross-linked hyaluronic acid occur simultaneously in step (b).

27. A process according to claim 25, wherein the activation of the cross-linked hyaluronic acid occurs prior to and separately from the coupling of the one or more dextran molecules to the activated cross-linked hyaluronic acid in step (b).

28. A process according to claim 25, wherein the coupling agent is selected from the group consisting of triazine-based coupling agents, carbodiimide coupling agents, imidazolium-derived coupling agents, Oxyma and COMU.

29. A process according to claim 28, wherein the coupling agent is a triazine-based coupling agent.

30. A process according to claim 29, wherein the triazine-based coupling agent is selected from the group consisting of 4-(4,6-dimethoxy-1,3,5-triazin-2-yl)-4-methylmorpholinium chloride (DMTMM) and 2-chloro-4,6-dimethoxy-1,3,5-triazine (CDMT).

31. A process according to claim 30, wherein the triazine-based coupling agent is DMTMM.

32. A hyaluronic acid product obtainable by the process according to claim 16.

33. A hyaluronic acid product according to claim 1 for use as a dermal filler.

* * * * *